United States Patent [19]

Bursuker et al.

[11] Patent Number: 5,147,799
[45] Date of Patent: Sep. 15, 1992

[54] REPOPULATION OF MACROPHAGES AND GRANULOCYTES USING TRANSFORMING GROWTH FACTOR-BETA

[76] Inventors: Isia Bursuker, 29 Currier Way, Cheshire, Conn. 06410; Joseph A. Carlino, 445 Hugo St. #5, San Francisco, Calif. 94122; Kim Neddermann, 183 Crestwood Dr., Naugatuck, Conn. 96770; Bernice Schacter, 748 Durham Rd., Madison, Conn. 06443; Larry Ellingsworth, 3566 Woodley Dr., San Jose, Calif. 95148; George Spitalny, 6 Brookfield Ct., Cheshire, Conn. 06410

[21] Appl. No.: 513,999

[22] Filed: Apr. 25, 1990

[51] Int. Cl.$^5$ .................. C12N 5/00; C07K 13/00; A61K 37/02
[52] U.S. Cl. .................. 435/240.1; 530/350; 514/12
[58] Field of Search .............. 435/240.1, 240.2; 530/351, 350

[56] References Cited

U.S. PATENT DOCUMENTS

| | | | |
|---|---|---|---|
| 4,774,322 | 12/1987 | Seyedin et al. | 530/353 |
| 4,806,523 | 2/1989 | Bentz et al. | 514/2 |
| 4,810,643 | 3/1989 | Souza | 435/68 |
| 4,833,127 | 5/1989 | Ono et al. | 514/21 |
| 4,843,063 | 6/1989 | Seyedin et al. | 514/2 |

OTHER PUBLICATIONS

Tessier et al., Transforming Growth Factor $\beta$ Inhibits the Proliferation of the Blast cells of Actue ..., blood, vol. 72, No. 1, pp. 159–164.
Roberts et al., *Proc. Natl. Acad. Sci. USA* (1985) 82:119–123.
Tsunawaki et al., *Nature* (1988) 334:260–262.
Goey et al., *J. Immunol.* (1989) 143(3):877–880.
Kawasaki et al., *Science* (1985) 230:291–296.
Stanley, *Methods Enzymol.* (1976) 116:564–578.
Seyedin, *J. Biol. Chem.* (1986) 261(13):5693–5695.
Gough, *Nature* (1984) 309:763–767.

*Primary Examiner*—John J. Doll
*Assistant Examiner*—George C. Elliott
*Attorney, Agent, or Firm*—Morrison & Foerster

[57] ABSTRACT

Treatment with Transforming Growth Factor-$\beta$ alone or in combination with a Colony Stimulating Factor therapeutically increases the number of granulocytes and monocyte/macrophages in mammals.

5 Claims, 3 Drawing Sheets

REPOPULATION OF MACROPHAGES AND GRANULOCYTES USING TRANSFORMING GROWTH FACTOR-BETA

DESCRIPTION

Technical Field

This invention relates to the fields of chemotherapy and regulation of hematopoiesis. More specifically, this invention relates to methods for increasing macrophage and granulocyte populations in an individual, particularly after chemotherapy.

BACKGROUND OF THE INVENTION

One of the primary distinguishing characteristics of cancer is the abnormally rapid division and proliferation of malignant cells. This is exploited in many current forms of chemotherapy, which have a greater effect on rapidly dividing cells than quiescent cells. Thus, normal, slowly dividing cells are less affected than malignant cells. Unfortunately, several cell types normally divide quickly, including the cells associated with hair follicles, intestinal lining, and hematopoiesis. The depression of hematopoiesis following chemotherapy is the most serious side effect, and in many cases leaves the patient susceptible to opportunistic infection due to the relative lack of lymphocytes, macrophages and granulocytes.

There are several known growth factors which are believed necessary for the induction and terminal differentiation of myeloid cells. Granulocyte-macrophage colony stimulating factor (GM-CSF) stimulates the formation of blast cells capable of differentiating into granulocytes (neutrophils and eosinophils) and macrophage/monocytes. Granulocyte colony stimulating factor (G-CSF) stimulates the production of granulocytes (predominantly neutrophils) from granulocyte/macrophage precursor cells. Macrophage colony stimulating factor (M-CSF) stimulates the production of monocyte/macrophages from granulocyte/macrophage precursor cells. Although it might seem a natural solution to administer GM-CSF, G-CSF, and/or M-CSF to patients undergoing chemotherapy, these cytokines may be effective only at toxic doses.

Seyedin, U.S. Pat. No. 4,774,322 filed Dec. 10, 1987, described two bovine bone-derived cartilage inducing factors (CIFs), designated CIF-A and CIF-B. Both have molecular weights of approximately 26,000 daltons by SDS-PAGE and are dimers. They each exhibit in vitro chondrogenic activity by themselves, as measured by cartilage specific proteoglycan (PG) production in an agarose gel culture model using fetal rat mesenchymal cells. Neither, however, is chondrogenically active in vivo by itself. Amino acid sequencing of the CIF-A showed that it has a partial (30 amino acids) N-terminal sequence identical to that reported for a human placenta-derived polypeptide called beta-type transforming growth factor (TGF-$\beta$). The partial N-terminal sequence of CIF-B is different from that of TGF-$\beta$. Both CIFs exhibit activity in the TGF-$\beta$ assay (ability to induce anchorage-independent growth of normal rat kidney cell colonies in soft agar). CIF-A/TGF-$\beta$ is now known by the name TGF-$\beta$1, while CIF-B is now generally referred to as TGF-$\beta$2.

TGF-$\beta$, when combined with EGF or TGF-alpha, (1) promotes cell proliferation in the soft agar culture assay and (2) promotes cell proliferation and protein deposition in a rat soft tissue wound healing model. The applications characterize the TGF-$\beta$s as being dimers having a molecular weight of approximately 26,000 daltons (26 kDa) by SDS-PAGE. TGF-$\beta$ exhibits a wide variety of activities, which appear to depend in large part to the cell type which is exposed. For example, TGF-$\beta$ stimulates growth of normal fibroblasts in the presence of EGF or TGF-$\alpha$, but inhibits the growth of some tumor cells: A. B. Roberts et al, *Proc Nat Acad Sci USA* (1985) 82:119–23. Bentz et al, U.S. Pat. No. 4,806,523, disclosed the use of TGF-$\beta$ (also known as CIF-A and CIF-B) to inhibit inflammation, and demonstrated that TGF-$\beta$ inhibited T-cell proliferation and antibody production. S. Tsunawaki et al, *Nature* (1988) 334:260–62 found that macrophages incubated with TGF-$\beta$1 or TGF-$\beta$2 were reversibly deactivated. H. Goey et al, *J Immunol* (1989) 143: 877–80 reported that administration of TGF-$\beta$1 directly to femoral bone marrow in mice in vivo reversibly suppressed the proliferation of pluripotential progenitor cells.

DISCLOSURE OF THE INVENTION

We have now invented a method for treating mammals in need of increased numbers of granulocytes and macrophages, by administering TGF-$\beta$ alone or in combination with a CSF. When TGF-$\beta$ is administered preceding or concurrently with a CSF, the effective dose required of CSF is reduced to subtoxic levels.

MODES OF CARRYING OUT THE INVENTION

A. Definitions

Figure 1:
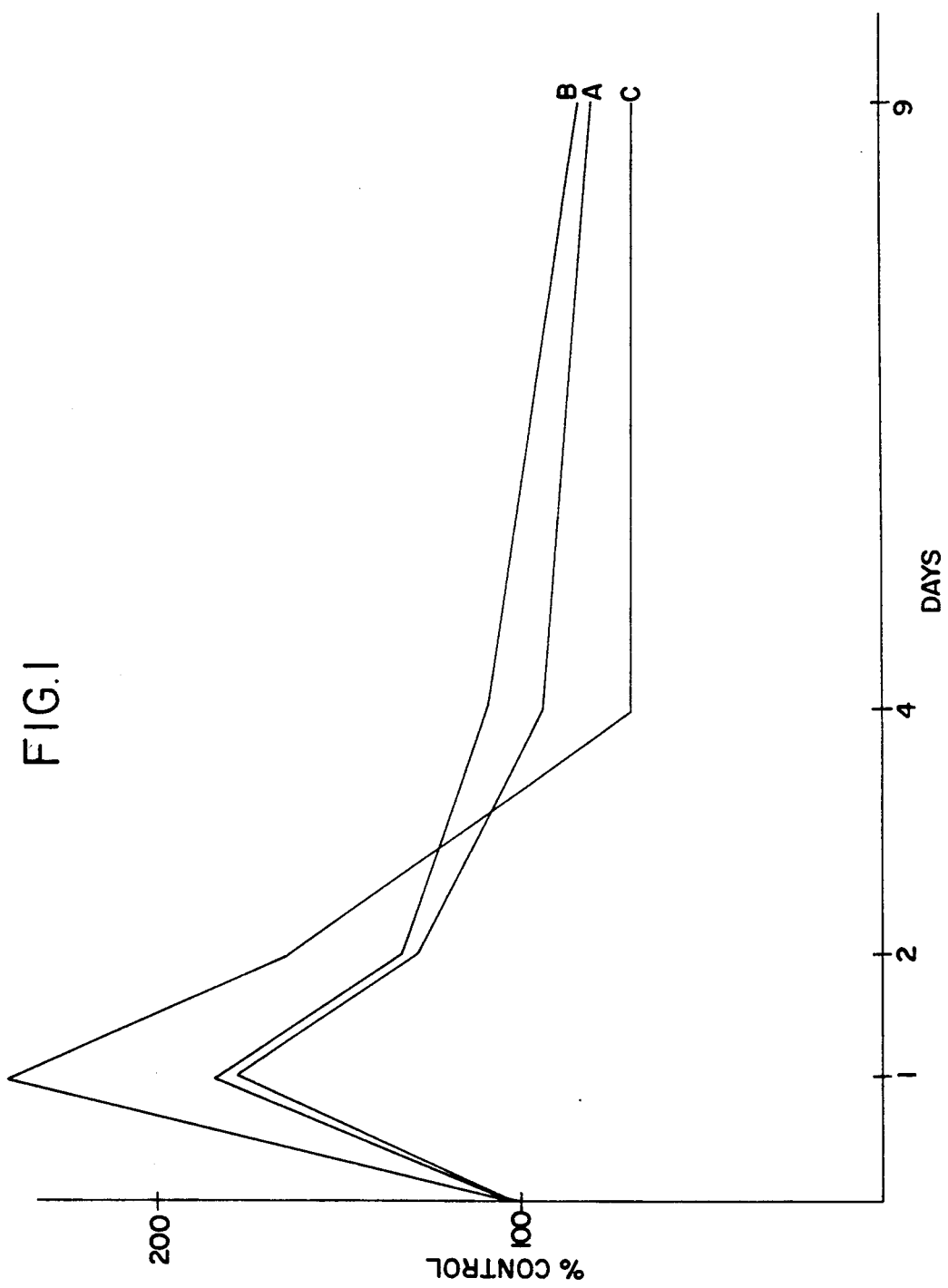
FIG. 1 depicts the increase in number of macrophages derived from bone marrow precursor cells of mice following in vivo administration of TGF-$\beta$1 followed by ex vivo administration of M-CSF, expressed as a percentage of control. The experiment is described in Example 1 below.

The term "TGF-$\beta$" or "transforming growth factor $\beta$" refers to the proteins TGF-$\beta$1, TGF-$\beta$2, and related proteins which are capable of binding to TGF-$\beta$ receptors and effecting TGF-$\beta$ type activity. In general, TGF-$\beta$ activity may be assessed by the observation of anchorage independent growth in fibroblasts in vitro, and the promotion of protein and connective tissue formation in wound healing models in vivo. "TGF-$\beta$" includes all TGF-$\beta$-like proteins, whereas "TGF-$\beta$1" and TGF-$\beta$2" indicate only those specific proteins as described under the names CIF-A and CIF-B in U.S. Pat. No. 4,774,322, incorporated herein by reference.

The term "CSF" refers to a colony stimulating factor, and includes proteins which are capable of inducing progenitor cells to differentiate toward granulocyte and macrophage/monocyte cell types. The presently preferred CSFs are M-CSF, GM-CSF, and G-CSF.

"Macrophage colony stimulating factor" or M-CSF is a heavily glycosylated homodimer of about 45 kDa which stimulates the growth of macrophage/monocyte cells from the appropriate precursor cells. Purification of M-CSF (also known as CSF-1) from natural sources was described by E. R. Stanley, *Meth Enzymol* (1985) 116:564-87, while cloning was disclosed by E. S. Kawasaki et al, *Science* (1985) 230:291-96; and Kawasaki et al, PCT WO86/04607.

"Granulocyte-macrophage colony stimulating factor" or GM-CSF is a glycoprotein of about 23 kDa which stimulates the growth of cells capable of differentiation to granulocytes (including neutrophils and eosinophils) and macrophage/monocyte cells from the appropriate precursor cells.

"Granulocyte colony stimulating factor" or G-CSF is a glycoprotein having a molecular weight of about 18 kDa, which stimulates the proliferation of neutrophil colonies. The partial N-terminal sequence is Thr-Pro-Leu-Gly-Pro-Ala-Ser-Ser-Leu-Pro-Gln-Ser-Phe-Leu-Leu-Lys-Cys-Leu-Glu-Gln. Purification of G-CSF from conditioned media is described by Ono et al, U.S. Pat. No. 4,833,127. Cloning and expression of G-CSF is described by Souza, U.S. Pat. No. 4,810,643.

B. General Method

TGF-$\beta$, GM-CSF, G-CSF, and M-CSF are all available from commercial sources or may be prepared from readily available materials using methods known to those skilled in the art, cited above.

TGF-$\beta$ and the selected CSF(s) are used either in vivo or ex vivo. TGF-$\beta$ is preferably administered in vivo. When administered in vivo, the proteins are generally introduced by parenteral routes, for example by intravenous injection, injection into the bone marrow, implanted device, intranasal aerosol, and the like. The presently preferred mode of in vivo administration is by intravenous injection.

The method of the invention is useful in any case wherein increased numbers of granulocytes and/or macrophages are desired, for example as the result of an immunosuppressive disorder, in treatment of infection or malignancy, or following treatment with agents having a myelosuppressive effect, whether intended or as a side effect. Suppression of granulopoiesis and myelopoiesis often occurs as a side effect in the treatment of malignancy with radiation or chemotherapeutic agents. This leaves the subject with an impaired ability to resist infection, often permitting opportunistic organisms to proliferate to a dangerous degree. In the practice of the invention, TGF-$\beta$ is administered near or following the time of treatment or disorder: preferably TGF-$\beta$ is administered between zero and five days following treatment. CSF is preferably administered only after chemotherapeutic or radiotherapeutic treatment, and is administered simultaneously with TGF-$\beta$ or up to four days later. CSF administration preferably follows TGF-$\beta$ administration by about 24-48 hours.

In the ex vivo methods of the invention, bone marrow (or other hematopoietic tissue) is removed from the subject (preferably) after administration of TGF-$\beta$, and the cells maintained in culture until treated with CSF.

Compositions of TGF-$\beta$, CSF, or combinations thereof for administration will generally include an effective amount of TGF-$\beta$ and/or CSF in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. A presently preferred vehicle comprises about 1 mg/mL serum albumin in phosphate-buffered saline (PBS). A thorough discussion of suitable vehicles for parenteral administration may be found in E. W. Martin, "Remington's Pharmaceutical Sciences" (Mack Pub. Co., current edition).

The precise dosage necessary will vary with the age, size, and condition of the subject, the nature and severity of the disorder to be treated, and the like: thus, a precise effective amount cannot be specified in advance. However, appropriate amounts may be determined by routine experimentation with animal models, as described below. In general terms, an effective dose of TGF-$\beta$ will range from about 10 $\mu$g/Kg to about 1 mg/Kg. The presently preferred TGF-$\beta$ is TGF-$\beta$1. An effective dose for M-CSF, GM-CSF, and/or G-CSF is about 10 $\mu$g/Kg to about 1 mg/Kg. Presently preferred CSFs are M-CSF and GM-CSF.

Suitable animal models include the mouse model illustrated in the Examples below. Briefly, TGF-$\beta$ is administered parenterally, followed 1-9 days later with extraction of the bone marrow. The marrow is diluted to a single-cell suspension and treated with CSF. The treated cells are allowed to proliferate and differentiate into macrophages and/or granulocytes, and the degree of proliferation and differentiation assayed by standard techniques (e.g., peroxide generation, $^3$H-thymidine incorporation, fluorescence-activated cell sorting (FACS), cell staining, and the like). The increased number (compared to controls) of granulocytes and/or macrophage/monocytes that results indicates the increased sensitivity to CSF by those precursor cells and may indicate increased number of precursor cells present due to TGF-$\beta$.

C. Examples

The examples presented below are provided as a further guide to the practitioner of ordinary skill in the art, and are not to be construed as limiting the invention in any way.

Example 1

Demonstration of Activity (A) Natural bovine TGF-$\beta$1 was dissolved in 0.25 mL of 4 mM HCl, then 0.75 mL of mouse serum albumin (MSA, 1 mg/mL) in phosphate buffered saline (PBS) added to make a 500 $\mu$g/mL TGF-$\beta$1 stock solution. From this solution, three experimental solutions were prepared by diluting the stock to 25 $\mu$g/mL, 50 $\mu$g/mL, and 125 $\mu$g/mL. A control solution was prepared identically, but omitting the TGF-$\beta$1.

(B) Sixty female C57Bl mice were divided into 5 experimental groups (12 mice per group) and injected subcutaneously with TGF-$\beta$1 (0.2 mL) on Day 0 as follows:

| | |
|---|---|
| A: | 5 $\mu$g TGF-$\beta$1 per mouse; |
| B: | 10 $\mu$g TGF-$\beta$1 per mouse; |
| C: | 25 $\mu$g TGF-$\beta$1 per mouse; |
| D: | untreated; |

| | |
|---|---|
| E: | treated with diluent. |

On day 1, 3 mice from each group were sacrificed, and bone marrow cells collected from the femur and tibia. This procedure is repeated on days 2, 4 and 9. Single cell suspensions were prepared in DMEM+10% horse serum and adjusted to $10^5$cells/mL, and plated in 24-well plates at 1.0 mL suspension/well. To each well was then added M-CSF (0.1 mL of a 500 U/mL stock), GM-CSF (0.1 mL of a 500 U/mL stock), or 0.1 mL PBS. The plates were then incubated for 6 days in a $CO_2$ humidified incubator, then washed with PBS and the cells fixed with formaldehyde. The fixed plates were washed with 0.1M borate buffer (pH 8.5), and stained with 1% methylene blue for 10 min. The stained plates were again washed with borate buffer, and allowed to air-dry. The stain was then eluted from the plates using 0.1N HCl for 20 min at 42° C., and the absorption of the eluent read at 630 nm.

Figure 2:
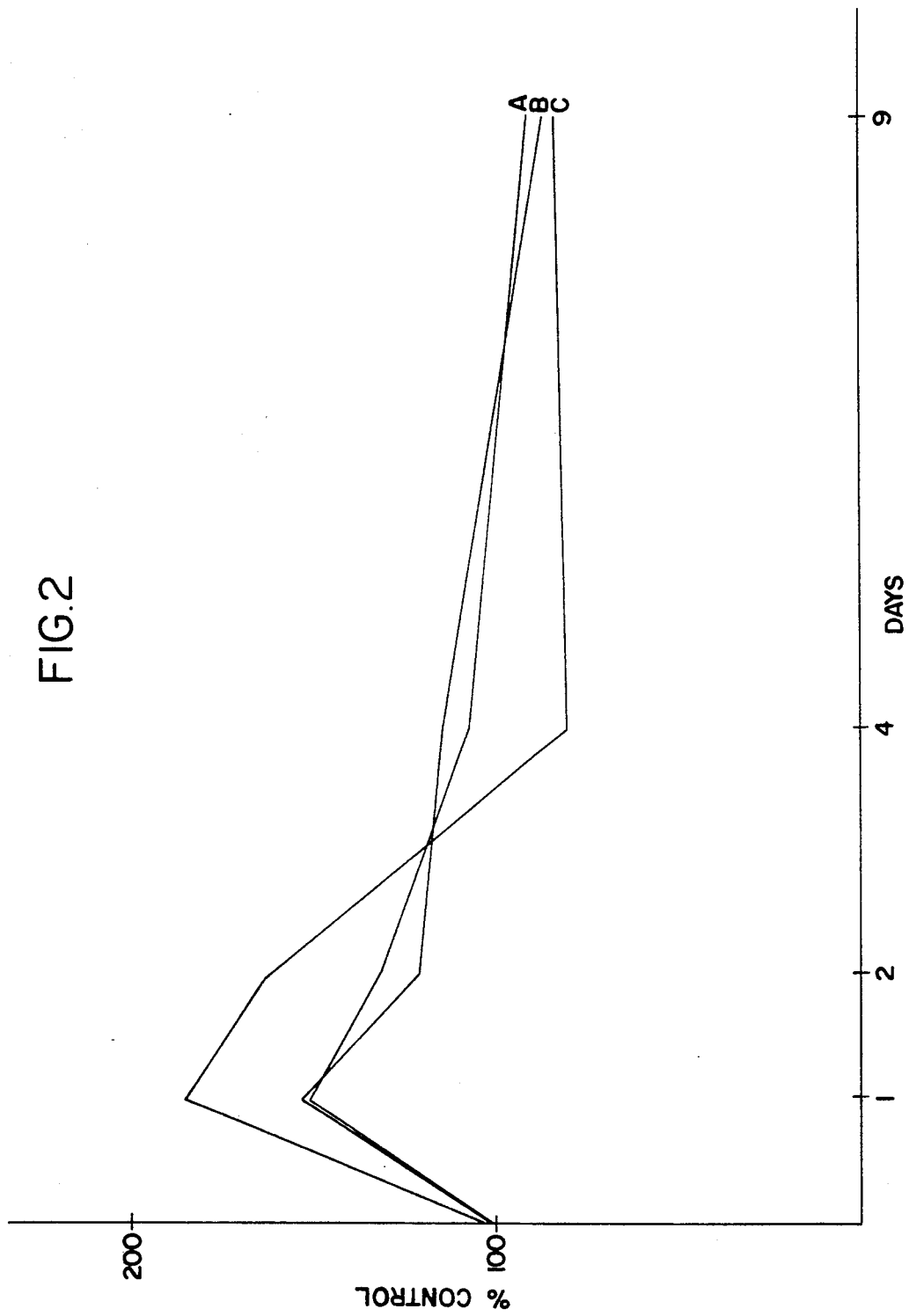
FIG. 2 depicts the increase in number of macrophages and granulocytes derived from bone marrow precursor cells of mice following in vivo administration of TGF-$\beta$1 followed by ex vivo administration of GM-CSF, expressed as a percentage of control. The experiment is described in Example 1 below.

The results are shown in FIGS. 1 and 2. FIG. 1 shows the increase in macrophage population resulting from the application of M-CSF to TGF-$\beta$1-induced marrow cells. Administration of 25 μg/mouse TGF-$\beta$1 increased macrophage number to about 240% of control on Day 1. This indicates that the number of macrophage precursor cells in the bone marrow was increased by the in vivo administration of TGF-$\beta$1. FIG. 2 illustrates the increased number of macrophages and granulocytes obtained by administration of GM-CSF, indicating the increased sensitivity GM precursor cells in bone marrow to CSF due to the in vivo administration of TGF-$\beta$1. The control groups were not affected.

EXAMPLE 2

(A) Fifteen male CB6F$_1$ mice were divided into 5 experimental groups (3 mice per group) and injected subcutaneously with TGF-$\beta$1 (0.2 mL) on Day 0 as follows:

| | |
|---|---|
| A: | Untreated; |
| B: | diluent control; |
| C: | 25 μg TGF-$\beta$1 per mouse; |
| D: | 10 μg TGF-$\beta$1 per mouse; |
| E: | 5 μg TGF-$\beta$1 per mouse. |

On day 2, the mice from each group were sacrificed, and bone marrow cells collected from the femur and tibia. Single cell suspensions were prepared in DMEM+10% horse serum and adjusted to $10^5$ cells/mL, and plated in 24-well plates at 1.0 mL suspension/well. Then, M-CSF (0.1 mL of a 500 U/mL stock), GM-CSF (0.1 mL of a 500 U/mL stock), or 0.1 mL PBS was added to each well. The plates were then incubated for 6 days in a $CO_2$ humidified incubator, then washed with PBS and the cells fixed with formaldehyde. The fixed plates were washed with 0.1 M borate buffer (pH 8.5), and stained with 1% methylene blue for 10 min. The stained plates were again washed with borate buffer, and allowed to air-dry. The stain was then eluted from the plates using 0.1N HCl for 20 min at 42° C, and the absorption of the eluent read at 630 nm.

The results are shown in Table 1 below. The results demonstrate that administration of TGF-$\beta$1 increased the sensitivity of macrophage and granulocyte precursor cells in bone marrow to CSF.

TABLE 1

| Group | % Untreated Control | % Diluent Control |
|---|---|---|
| A: Untreated | 100.0 | — |
| B: Diluent | 100.0 | — |
| +M-CSF | 88.7 | — |
| +GM-CSF | 114.6 | — |
| C: 25 μg TGF-$\beta$1 | | |
| +M-CSF | 161.3 | 181.9 |
| +GM-CSF | 201.6 | 175.8 |
| D: 10 μg TGF-$\beta$1 | | |
| +M-CSF | 166.4 | 187.6 |
| +GM-CSF | 193 | 168.3 |
| E: 5 μg TGF-$\beta$1 | | |
| +M-CSF | 177.5 | 200.2 |
| +GM-CSF | 218.8 | 190.8 |

Figure 3:
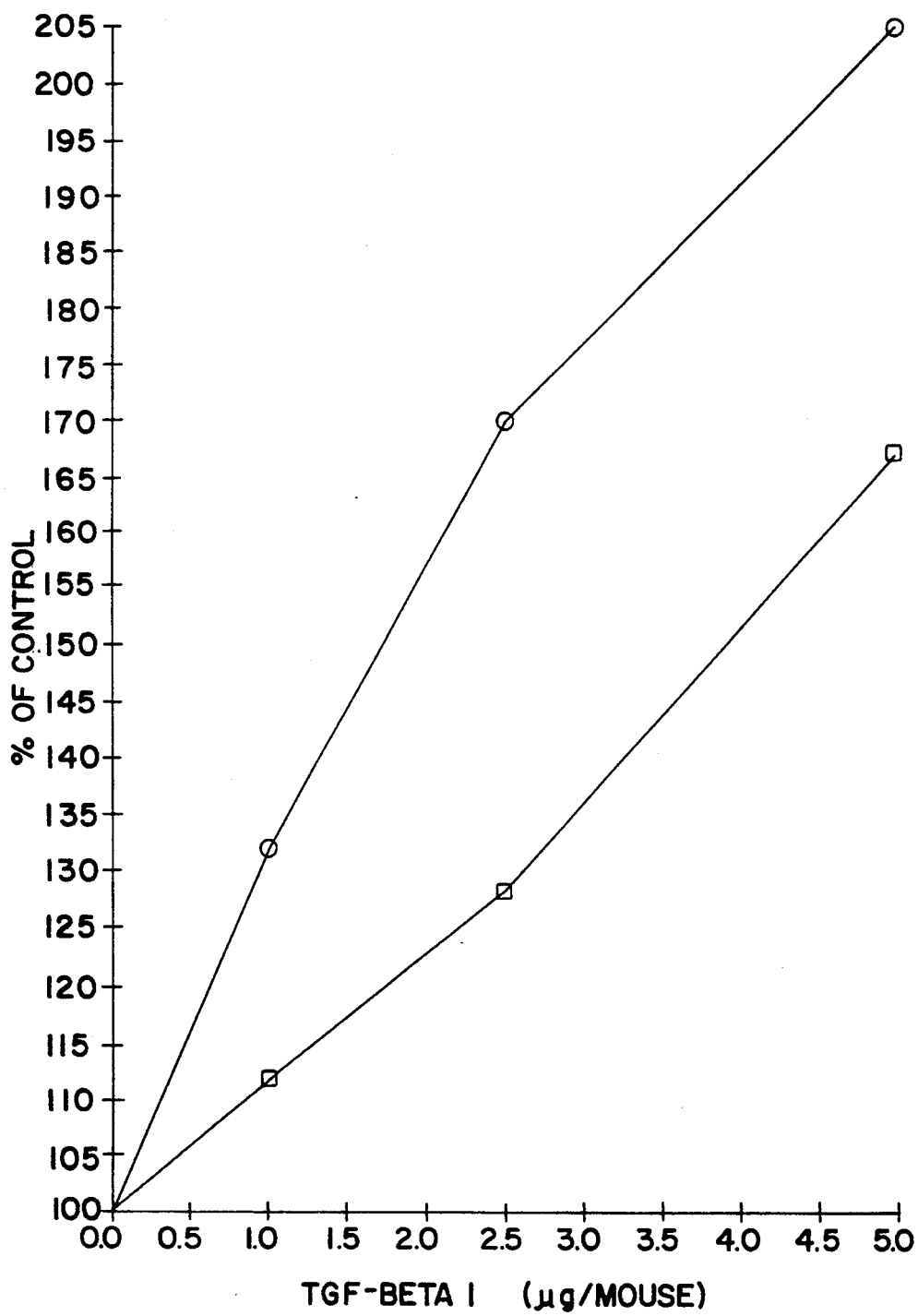
FIG. 3 depicts the dose-dependent increase in number of macrophages and granulocytes derived from bone marrow precursor cells of mice following in vivo administration of TGF-$\beta$1 followed by ex vivo administration of GM-CSF, expressed as a percentage of control. The experiment is described in Example 2(B) below.

(B) The experiment of part (A) above was repeated, substituting doses of 1.0, 2.5, and 5.0 μg/mouse TGF-$\beta$. The results are shown in FIG. 3, expressed as percent of control. A dose-dependent response was observed.

EXAMPLE 3

Mode of Administration

This experiment was performed to determine if the mode of administration affected the biological response.

Twelve male CB6F$_1$ mice were divided into 5 experimental groups (3 mice per group) and injected subcutaneously with TGF-$\beta$1 (0.2 mL) on Day 0 as follows:

| | |
|---|---|
| A: | Untreated; |
| B: | 25 μg TGF-$\beta$1 per mouse, subcutaneous; |
| C: | 25 μg TGF-$\beta$1 per mouse, intravenous; |
| D: | 25 μg TGF-$\beta$1 per mouse, intraperitoneal. |

On day 2, the mice from each group were sacrificed, and bone marrow cells collected from the femur and tibia. Single cell suspensions were prepared in DMEM +10% horse serum and adjusted to $10^5$ cells/mL, and plated in 24-well plates at 1.0 mL suspension/well. M-CSF (0.1 mL of a 500 U/mL stock), GM-CSF (0.1 mL of a 500 U/mL stock), or 0.1 mL PBS was added to each well. The plates were then incubated for 6 days in a $CO_2$ humidified incubator, then washed with PBS and the cells fixed with formaldehyde. The fixed plates were washed with 0.1M borate buffer (pH 8.5), and stained with 1% methylene blue for 10 min. The stained plates were again washed with borate buffer, and allowed to air-dry. The stain was then eluted from the plates using 0.1N HCl for 20 min at 42° C., and the absorption of the eluent read at 630 nm.

The results are shown in Table 2 below. The results demonstrate that the biological effect is independent of route of administration.

TABLE 2

| Group | % Untreated Control |
|---|---|
| A: Untreated | 100.0 |
| B: subcutaneous (thigh) | |
| +M-CSF | 194.7 |
| +GM-CSF | 195.2 |
| C: intravenous | |
| +M-CSF | 217 |
| +GM-CSF | 213.5 |
| D: intraperitoneal | |
| +M-CSF | 218.1 |
| +GM-CSF | 214.4 |

What is claimed:

1. A method of inducing the proliferation and differentiation of mammalian granulocytes or monocyte/macrophages, comprising the steps of:
   administering to a mammal having hematopoietic stem cells, an effective amount of TGF-β selected from the group consisting of TGF-β1 and TGF-β2, the TGF-β being administered such that a sufficient amount contacts the hematopoietic stem cells to affect hematopoietic stem cell growth or differentiation;
   removing the hematopoietic stem cells affected by the TGF-β from the mammal; and
   contacting the removed cells with an effective amount of a CSF selected from the group consisting of M-CSF, G-CSF and GM-CSF, the removed cells being contacted with a sufficient amount of CSF to stimulate the formation of granulocytes and/or monocyte/macrophages.

2. The method as claimed in claim 1, wherein the removed hematopoietic cells are contacted with the CSF at a period of time about 1-2 days after contact with the TFG-β.

3. A kit for inducing granulocyte, monocyte/macrophage proliferation and differentiation, comprising:
   a container having therein a therapeutically effective amount of TGF-β dispersed in a pharmaceutically acceptable carrier, the TGF-β being present in an amount sufficient to affect the growth of hematopoietic stem cells; and
   a second container having therein a therapeutically effective amount of CSF dispersed throughout a pharmaceutically acceptable carrier, the CSF being present in an amount so as to stimulate proliferation and differentiation of granulocytes and/or monocytes/macrophages.

4. The kit as claimed in claim 3, wherein the TGF-β is TGF-β1.

5. The kit as claimed in claim 3, wherein the CSF is selected from the group consisting of M-CSF, G-CSF and GM-CSF.

* * * * *